United States Patent [19]

Williams

[11] Patent Number: 5,338,834
[45] Date of Patent: Aug. 16, 1994

[54] ULTRAPURE HUMAN INTERLEUKIN-6

[75] Inventor: Ashley M. Williams, Mississauga, Canada

[73] Assignee: Allelix Biopharmaceuticals Inc., Mississauga, Canada

[21] Appl. No.: 9,973

[22] Filed: Jan. 26, 1993

[51] Int. Cl.$^5$ .......................... C07K 3/02; C07K 3/20; C07K 3/22; C07K 15/06
[52] U.S. Cl. ................................... 530/351; 530/412; 530/415; 530/416; 530/417
[58] Field of Search ............... 530/351, 412, 415, 416, 530/417; 424/85.2

[56] References Cited

FOREIGN PATENT DOCUMENTS

| | | |
|---|---|---|
| 0220574 | 5/1987 | European Pat. Off. . |
| 0257406 | 3/1988 | European Pat. Off. . |
| 0413908 | 2/1991 | European Pat. Off. . |
| 0504751 | 9/1992 | European Pat. Off. . |
| 0550756 | 7/1993 | European Pat. Off. . |
| 2063882 | 5/1984 | United Kingdom . |
| 88/00206 | 1/1988 | World Int. Prop. O. . |
| 90/06370 | 6/1990 | World Int. Prop. O. . |
| 9218537 | 10/1992 | World Int. Prop. O. . |

OTHER PUBLICATIONS

Harris, E. L. V. & S. Angal "Protein Purification Methods" 1989 pp. 230–232.

Gordon et al., "Capillary Electrophoresis", Science, Oct. 14, 1988, vol. 242, pp. 224–228.

Van Damme et al., "Purification And Characterization Of Human Fibroblast-Derived Hybridoma Growth Factor Identical To T-Cell derived B-Cell Stimulatory Factor-2 (Interleukin-6)", Eur. J. Biochem., 168, Feb. 1987, pp. 543–550.

Lee et al., "A Multifunctional Regulator Of Growth And Differentiation", Annals New York Academy Of Sciences, 1989, vol. 557, pp. 215–229.

Aarden et al., "Production Of Hybridoma Growth Factor By Human Monocytes", Eur. J. Immunol, #17, 1987, pp. 1411–1416.

Contreras et al., "Efficient Kex2-Like Processing Of aA Glucoamylase-Interleukin-6 Fusion Protein By Aspergillus Nidulans And Secretion Of Mature Interleukin-6", Bio/Technology, vol. 9, Apr. 1991, pp. 378–381.

Guisez et al., "Production And Purification Of Recombinant Human Interleukin-6 Secreted By The Yeast Saccharomyces Cerevisiae", Eur. J. Biochem., 198, Jan. 1991, pp. 217–222.

Hirano et al., "Purification To Homogeneity And Characterization Of Human B-Cell Differentiation Factor (BCDF Or $BSF_p$-2)", Proc. Natl. Acad. Sci., vol. 82, pp. 5490–5494.

Matsuura et al., "Biological Function Of Recombinant IL-6 Expressed In a Baculovirus System", Lymphokine And Cytokine Research, vol. 10, No. 3, 1991, pp. 201–205.

Arcone et al., "Single-Step Purification And Structural Characterization Of Human Interleukin-6 Produced In Escherichia Coli From A T7 RNA Polymerase Expression Vector", Eur. J. Biochem, 198, Feb. 1991, pp. 541–547.

Parekh et al., "Glycosylation Of Interleukin-6 Purified From Normal Human Blood Mononuclear Cells", Eur. J. Biochem., 203, Feb. 1992, pp. 135–141.

(List continued on next page.)

Primary Examiner—Jeffrey E. Russel
Assistant Examiner—Nancy J. Gromet
Attorney, Agent, or Firm—Foley & Lardner

[57] ABSTRACT

Essentially pure human interleukin-6 having a purity of at least 98 % as determined by single peak migration using capillary electrophoresis is obtained by a 3-step purification method which includes a cation-exchange chromatography step, a hydrophobic chromatography step and a reverse-phase chromatography step in the presence of a charge modifier.

10 Claims, 4 Drawing Sheets

OTHER PUBLICATIONS

Brakenoff et al., "Molecular Cloning And Expression Of Hybridoma Growth Factor In Escherichia Coli", The Journal Of Immunology, No. 12, Dec. 15, 1987, pp. 4116–4121.

Asagoe et al., "Human B–Cell Stimulatory Factor–2 Expressed In Escherichia Coli", Bio/Technology, Jul. 6, 1988, pp. 806–809.

Revel et al., "Biological Activities Of Recombinant Human IFN-$\beta$2/IL-6(E. coli)", Annals New York Academy of Sciences, vol. 557, 1987, pp. 144–156.

Sofer et al., "Designing An Optimal Chromatographic Purification Scheme For Proteins", Bio Techniques, Nov./Dec. 1983, pp. 198–203.

Nurse et al., "Isolation Of A Monoclonal Antibody To The TrpE Protein And Its Use For The Purification Of Recombinant Fusion Proteins", Hybridoma, vol. 10, No. 6, 1991, pp. 753–760.

Epstein, "High Level Expression And Purification Of Human Recombinant Interleukin-6 (IL-6)", Exper. Hematology, vol. 18, No. 6, 1990, p. 716 Sec. 639.

FIG. 1

```
                                  Val Pro Pro Gly Glu Asp Ser Lys Asp
GTA GCC GCC CCA CAC AGA CAG CCA CTC ACC TCT TCA GAA CGA ATT GAC AAA CAA ATT
Val Ala Ala Pro His Arg Gln Pro Leu Thr Ser Ser Glu Arg Ile Asp Lys Gln Ile

CGG TAC ATC CTC GAC GGC ATC TCA GCC CTG AGA AAG GAG ACA AAG TGT AAC AGT AAC
Arg Tyr Ile Leu Asp Gly Ile Ser Ala Leu Arg Lys Glu Thr Lys Cys Asn Ser Asn

ATG TGT GAA AGC AGC AAA GAG GCA CTG GCA GAA AAC CTT CCA AAC AAG ATG
Met Cys Glu Ser Ser Lys Glu Ala Leu Ala Glu Asn Leu Pro Lys Met

GCT GAA AAA GAT GGA TGC TTC CAA TCT GGA TTC AAT GAG ACT TGC CTG GTG AAA
Ala Glu Lys Asp Gly Cys Phe Gln Ser Gly Phe Asn Glu Thr Cys Leu Val Lys

ATC ATC ACT GGT CTT TTG GAG TTT CTT GAG GTA TAC CTA GAG TAC CTC CAG AAC AGA TTT
Ile Ile Thr Gly Leu Leu Glu Phe Glu Val Tyr Leu Glu Tyr Leu Gln Asn Arg Phe

GAG AGT AGT GAG GAA CAA CAA GCC AGA GCT GTG CAG ATG AGT ACA AAA GTC CTG ATC CAG
Glu Ser Ser Glu Glu Gln Gln Ala Arg Ala Val Gln Met Ser Thr Lys Val Leu Ile Gln

TTC CTG CAG AAA AAG GCA AAG AAT CTA GAT GCA ATA ACC ACC ATA ACC CCT GAC CCA ACC ACA
Phe Leu Gln Lys Lys Ala Lys Asn Leu Asp Ala Ile Thr Thr Pro Asp Pro Thr Thr

AAT GCC AGC CTG CTG ACG AAG CTG CAG AAC CAG CTG CTG CAG GAC ATG ACA
Asn Ala Ser Leu Leu Thr Lys Leu Gln Asn Gln Trp Leu Gln Asp Met Thr

ACT CAT CTC ATT CTG CGC AGC TTT AAG GAG TTC CTG CAG TCC AGC CTG AGG GCT CTT
Thr His Leu Ile Leu Arg Ser Phe Lys Glu Phe Leu Gln Ser Ser Leu Arg Ala Leu

CGG CAA ATG TAG
Arg Gln Met End
```

ULTRAPURE HUMAN INTERLEUKIN-6

FIELD OF THE INVENTION

The present invention relates to human interleukin-6, and more particularly, to essentially pure human interleukin-6 and a method of obtaining essentially pure human interleukin-6.

BACKGROUND OF THE INVENTION

Interleukin-6, also known as interferon-β2 (IFN-β2), B-cell stimulating factor, hepatocyte stimulating factor and hybridoma growth factor, is a multifunctional cytokine secreted by a variety of cells including monocytes, leukocytes, hepatocytes, fibroblasts, epithelial cells, endothelial cells, glial cells, cardiac myxoma tissue and some bladder carcinomas and cervical cancer cells. Interleukin-6 (hereinafter also referred to as IL-6) regulates the growth and differentiation of many of these cells and appears to play an important role in mediating response to viral and bacterial infections and to shock. Thus, IL-6 has the potential to become a clinically significant compound having multiple therapeutic indications including the treatment of bacterial infection, viral infection and inflammation, and application as an antitumour agent.

The effective clinical use of IL-6 is dependent on, among other things, the provision of IL-6 in a form of pharmaceutically acceptable purity. The purity of a compound for use in a pharmaceutical composition is known to affect the level of its biological activity. Accordingly, as the purity of a compound approaches 100%, its level of biological activity per unit dose is maximized and the compound becomes more pharmaceutically effective. Purity may also impact on the incidence of undesirable side effects associated with the administration of a pharmaceutical compound. Often the identity of impurities which contaminate a compound are unknown and, as a result, the effects upon administration cannot be predetermined. The provision of a pharmaceutical compound in essentially pure form will circumvent the occurrence of complications that may arise from impurities.

One method commonly used to purify proteins is reversed phase high performance liquid chromatography (RP-HPLC). In general, liquid chromatography exploits the variable rates at which proteins migrate in a two phase liquid solvent system through a column typically consisting of silica gel particles. In reversed phase HPLC, a polar mobile phase and a non-polar stationary phase solvent system is utilized to effect separation and thus purification of a protein sample. Typically, the mobile phase consists of water and an organic solvent combined with an ion-pairing agent or charge modifier. The relative proportions of the water and organic solvent in the mobile phase may be altered gradiently over the course of the protein migration through the silica column in order to augment the analysis. A protein preparation eliciting a single peak when analyzed using liquid chromatography (as identified by UV absorbance at a wavelength of 214 nm or 280 nm) was heretofore believed to consist of a single protein species and has previously been characterized as being essentially pure.

However, the sensitivity of such HPLC techniques has been found to be secondary to the sensitivity of the method of capillary electrophoresis in analyzing the purity of a protein sample. Capillary electrophoresis separates proteins based on their mass/charge ratio within a capillary having a bore of miniscule diameter, as described by Gordon et al. in Science, 1988, 242:224. Briefly, aqueous samples of a protein preparation to be analyzed are drawn by vacuum into the capillary and subjected to an electric field. Migration of the protein species through the capillary is monitored by detecting UV absorbance, usually at 214 nm. Protein samples determined to be essentially pure by HPLC have subsequently been analyzed by capillary electrophoresis, the results of which reveal that, in fact, the sample contains more than one compound as indicated by the occurrence of more than one absorption peak, and thus is not essentially pure as originally determined.

Reversed phase HPLC has been used previously as a step in the purification of IL-6. Van Damme et al. (Eur. J. Biochem, 1987, 168:543) describe a 5-step purification process for IL-6 produced from human fibroblast cultures. The purification steps included in the process were silicic acid adsorption, antibody affinity chromatography, gel filtration chromatography, cation-exchange chromatography and reverse-phase HPLC. The process was described as yielding pure IL-6 as determined using the method of gel electrophoresis, i.e. approximately pure IL-6.

Methods for making and purifying recombinantly-produced interleukin-6 have also been described in the art. For example, recombinantly produced murine IL-6 has been purified by ultrafiltration followed by fractionation using reverse phase liquid chromatography initially under acidic conditions and then under alkaline conditions as described by Lee et al. (Ann. NY Acad. Sci. 1989, 557:215). A further method of providing recombinant IL-6 has been described by Clark et al. in WO 88/00206. In particular, this reference teaches a method for the bacterial production of non-glycosylated IL-6, a form of IL-6 which does not naturally exist in humans. In both cases IL-6 is provided, as in the process of Van Damme, supra, in a form estimated to be pure by gel electrophoresis.

To date, essentially pure human interleukin-6, as indicated by single peak absorption using capillary electrophoresis, and a method for obtaining such essentially pure human interleukin-6 has not been reported.

Thus, an object of the present invention is to provide human IL-6 in essentially pure form, free from contaminants detectable by capillary electrophoresis (CE). A further object of the present invention is to provide a method to obtain such essentially pure human IL-6.

SUMMARY OF THE INVENTION

The present invention provides essentially pure human interleukin-6 as determined by single peak absorbance using the technique of capillary electrophoresis.

Thus, in one aspect of the present invention, there is provided a method for obtaining essentially pure human interleukin-6 comprising the steps of:

1) fractionating a preparation containing human interleukin-6 by cation-exchange chromatography using a column comprising a cationic resin, and eluting from said column a first interleukin-6 sample;
2) fractionating said first interleukin-6 sample by hydrophobic chromatography using an adsorption column comprising a hydrophobic adsorbent, and eluting from said adsorption column a second interleukin-6 sample; and 3) fractionating said second interleukin-6 sample by reverse-phase high performance liquid chromatography in the presence of a charge modifier.

In a further aspect of the present invention, them is provided a pharmaceutical composition comprising a therapeutically effective amount of essentially pure interleukin-6 in combination with a pharmaceutically acceptable carrier.

These and other aspects of the present invention are described herein in greater detail by reference to the following Figures in which:

BRIEF REFERENCE TO THE DRAWINGS

FIG. 1 illustrates the nucleotide (SEQ ID NO:2) and amino acid (SEQ ID NO:1) sequence of human interleukin-6;

DETAILED DESCRIPTION OF THE INVENTION

Figure 2:
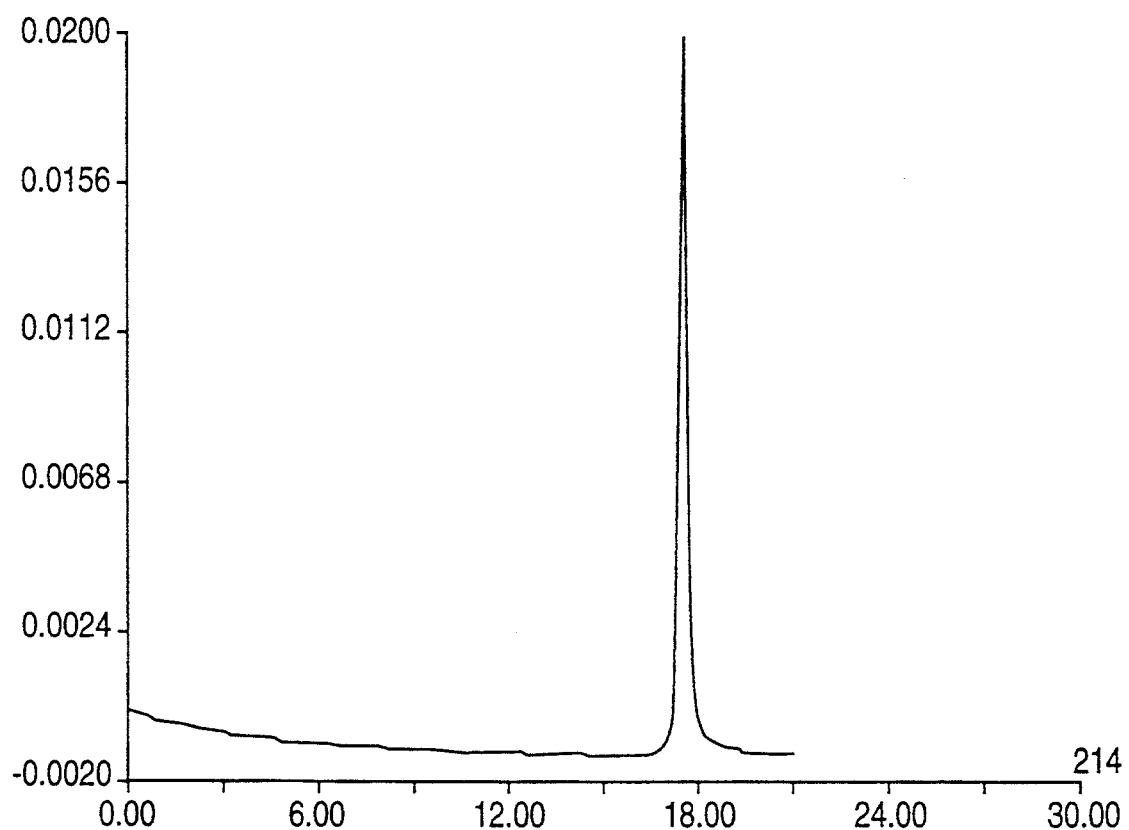
FIG. 2 represents the absorbance ($A_{214}$) capillary electrophoretic profile of essentially pure human interleukin-6 obtained using triethylamine phosphate-based RP-HPLC.

The present invention provides essentially pure human interleukin-6 as evidenced by migration of a single absorbance peak at 214 nm using the technique of capillary electrophoresis. The term "essentially pure", thus, is used herein with respect to human interleukin-6 to encompass human interleukin-6 which is free from contaminating substances detectable at 214 nm by capillary electrophoresis, i.e. human IL-6 having a purity of at least 98%, and preferably having a purity of greater than 99%.

The terms human interleukin-6, human IL-6 and hIL-6 are used interchangeably herein to denote a protein having the amino acid sequence set out in FIG. 1 (SEQ ID NO:1). It will be appreciated by those of skill in the an that slight variations in the amino acid structure of human IL-6 may occur which are also within the scope of the present invention. Such variations may occur as a result of the source of the IL-6. For example, synthetic hIL-6 may include a small proportion of oxidized IL-6 or may incorporate amino acids beating protecting groups on some alpha carbon side chains. Such modifications of the IL-6 structure are encompassed to the extent that they are undetectable in an hIL-6 sample analyzed by capillary electrophoresis in the manner herein exemplified.

Essentially pure human IL-6 in accordance with the present invention is characterized in particular by single peak absorption at 214 nm when analyzed by capillary electrophoresis. Single peak absorption by capillary electrophoretic analysis indicates that the hIL-6 has a purity approaching 100% and is at least at a purity level of 98%, preferably at a purity level of greater than 99%. To analyze a human IL-6 sample by capillary electrophoresis to determine if the sample contains essentially pure hIL-6, the sample is prepared in a suitably buffered aqueous vehicle, for example, a phosphate buffer of pH 2–3, at a concentration in the approximate range of about 0.2 mg/ml to about 1.0 mg/ml. The sample is then loaded onto a capillary of suitable dimensions, such as 50 cm $\times$ 50 $\mu$ M. The rate at which the sample is loaded onto the capillary is uniform, and is generally in the range of about 2 to 10 seconds. It is most desirable to load the sample onto the capillary as rapidly as possible, particularly a sample that may contain volatile contaminants, to avoid loss of such contaminants to the atmosphere. Generally, a 5–10 ng load of IL-6 sample is sufficient to enable detection of contaminants within the sample on the capillary electrophoretic absorbance profile.

Essentially pure hIL-6 is also characterized by exceptional bioactivity as determined using the B9 cell proliferation assay described by Aarden et al., Eur. J. Immunol. 1987 17:1411, which is incorporated herein by reference. The B9 cell assay measures quantitatively the extent to which a given concentration of interleukin-6 stimulates immunoglobulin production (IgM) as indicated by uptake of tritiated thymidine. Essentially pure hIL-6 according to the present invention has an activity of at least $5 \times 10^8$ international units/rag (IU/mg) of protein using the B9 cell assay. The measurement of international units indicates that the results of the activity assay are based on a comparison with an international standard obtained from the National Institute for Biological Standards and Control.

Human IL-6 to be purified in accordance with the method of the present invention is not particularly restricted and may be obtained from any one of numerous sources. As indicated in the foregoing, the hIL-6 to be purified to essentially pure hIL-6 as herein defined may be synthetically-derived using established recombinant methods. Such methods generally entail transformation of a suitable prokaryotic or eukaryotic host cell with a vector having inserted expressibly therein the DNA sequence encoding hIL-6. Thus, recombinant hIL-6 may be derived from any suitable microbial source including bacterial sources such as *E. coli* and *B. subtilis*, fungal sources such as *Aspergillus nidulans* and *Aspergillus niger* and yeast sources. Eukaryotic cell lines may also be employed to produce hIL-6 including insect cell lines such as *Spodoptera frugiperda* and mammalian cell lines such as Chinese hamster ovary cells (CHO cells) for example of K1 lineage (ATCC CCL 61) including the Pro5 variant (ATCC CRL 1281); fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including HeLA lineage (ATCC CCL 2) and neuroblastoma cells of the lines IMR-32 (ATCC CCL 127), SK-N-MC (ATCC HTB 10) and SK-N-SH (ATCC HTB 11). Alternatively, human IL-6 may be isolated from a biological sample as described by Van Damme et al., supra.

As will be appreciated by one of skill in the art, depending on the source, the human IL6 may or may not be modified post-translationally, and thus may or may not be glycosylated by N- and O-glycans, or phosphorylated, so as to be in the form in which it naturally exists in humans. Human IL-6 produced from mammalian cell lines is glycosylated while other sources of hIL-6 including bacterial, fungal and yeast cell sources produce non-glycosylated hIL-6.

In one embodiment of the present invention, non-glycosylated hIL-6 derived from the fungal source, *Aspergillus nidulans*, is purified to an essentially pure form using the present method. As described in more detail in the specific examples herein, *A. nidulans* has been engineered genetically to produce hIL-6 as an extracellular, non-glycosylated product, and medium conditioned by culturing thereof represents a suitable source of hIL-6 for subsequent purification. Particularly, upon completion of the fermentation, the hIL-6-containing fungal broth is separated from the fungal cellular mass by filtration. The pH and conductivity of the filtrate are adjusted, for example to about 4.5 and 8.0 Ms/cm respectively, and then the treated broth is fractionated using the present method to render essentially pure human interleukin-6 as determined by subsequent capillary electrophoresis analysis.

In one embodiment, purification is achieved using a three-step method, each step of which separates hIL-6 in a given sample from contaminants therein based on a particular property of hIL-6. Included in the steps of the method as a first step is fractionation of the sample using cation-exchange chromatography. A second step of the hIL-6 purification method is fractionation by hydrophobic chromatography followed by a third reverse-phase high performance liquid chromatography (RP-HPLC) step.

Initially, an hIL-6 sample may be fractionated using ion-exchange chromatography, a technique which separates proteins by differences in their acid-base properties using a column filled with granules of a synthetic resin. The resin incorporates charged groups which bind oppositely charged groups on substances in the sample; for example, when the charged group on the resin is cationic, anionic groups on proteins in the sample are exploited to effect their separation. Bound proteins are eluted from the column with an elution buffer of pH or ionic strength suitable to displace the proteins, and in the case of a cationic resin, a buffer having an increased pH or a buffer containing anions is used for the elution. The resin is selected such that it is capable of separating the desired protein or proteins from other components in a sample by selectively binding these proteins. In the purification of hIL-6, cation exchange chromatography is utilized to separate hIL-6 from other components that may be present in the hIL-6-containing sample. Thus, an appropriate resin for use in purifying hIL-6 is a resin having cationic groups attached thereto, or a cation exchange resin. Particularly appropriate resins for use in fractionating proteins are resins of derivatized cellulose, dextran, agarose and synthetic polymers such as trisacryl. In this regard, examples of suitable cationic resins for hIL-6 purification are carboxymethyl derivatives of cellulose, dextran, agarose (i.e. trademark "Sepharose") and trisacryl, phosphocellulose, and sulfopropyl- and sulfoethyl- derivatives of cellulose, agarose and dextran. A preferred resin is sulfopropyl-agarose (trademark "S-Sepharose").

The column of cationic exchange resin is equilibrated, prior to its use in purifying hIL-6, with an equilibration buffer having a pH equal to the pH of the hIL-6 protein sample to be processed. Generally, column equilibration comprises running a number of column volumes of the equilibration buffer through the column until the buffer collected from the column has a constant pH and conductivity. The sample, up to an amount of about 15–20 mg of protein per milliliter of resin, is loaded onto the equilibrated column and buffer, usually the equilibration buffer, is run through the column until the desired hIL-6 protein is separated from the other components of the protein sample, as indicated by a particular property of the eluting buffer such as its absorbance at 280 nm. The resolved hIL-6 is then eluted from the column with an anionic elution buffer having at least one of a distinct pH or ionic strength from the equilibration buffer in order to successfully displace the resolved proteins from the resin. Suitable anionic elution buffers include phosphate, sulphate or acetate buffers. Gradient elution, in which the composition of the anionic elution buffer is gradually altered, i.e. the pH, ionic strength or anion content of the elution buffer is altered, during the course of the elution, may also be used to elute hIL-6 from the cation-exchange column.

In a specific embodiment of the present invention, cation-exchange chromatography using a sulfopropyl-agarose resin is employed in the first step of hIL-6 purification. The column is equilibrated with an acetate buffer of pH 4.5 prior to loading the hIL-6 sample onto the column. Acetate buffer of pH increasing from pH 4.5 is used to separate the hIL-6 from contaminating components in the sample until the UV absorbance of the buffer eluting from the column at 280 nm approaches zero. Human IL-6 is subsequently eluted from the column using a phosphate elution buffer increased two-fold in ionic strength from the ionic strength of the equilibration buffer and having an increased pH of 7.5. The elution buffer passing through the column is collected in fractions and those fractions containing IL-6 are determined by UV absorbance at 280 nm. About 10 column volumes of buffer following loading of the sample are required to elute hIL-6 from the cation-exchange column under these conditions. The identity of IL-6 is confirmed using any one of a number of methods including RP-HPLC or sodium dodecylsulphate (SDS) gel electrophoresis analysis by reference to the result obtained using a known human interleukin-6 standard.

The IL-6-containing fractions from the cation-exchange step are combined and subjected to a second purification step of the present method, specifically, hydrophobic chromatography, a technique used to separate proteins based on their selective adsorption to a relatively inert particulate adsorbent matrix, such as charcoal, silica gel, alumina, hydroxyapatite and agarose, as they are passed through a column packed with the adsorbent material. The exact nature of the forces acting to adsorb the protein to the particulate adsorbent are not known but presumably any of van der Waals forces, hydrophobic interactions, ionic attractions and hydrogen binding may play a role in the adsorption. As in ion-exchange chromatography, an elution buffer of appropriate ionic strength is used to displace proteins adsorbed to the adsorbent.

To effect further purification of an hIL-6 sample by hydrophobic chromatography, suitable hydrophobic adsorbents are chosen which selectively adsorb hIL-6, and thus, are effective in separating IL-6 from other components in the sample. In this step, the hydrophobic nature of the hIL-6 molecule is exploited to retain hIL-6 on the column while other components are not retained and thus elute from the column. Appropriately substituted adsorbents for use include those having a hydrophobic group bonded thereto such as linear aliphatic $C_4$, $C_8$, $C_{10}$ and $C_{18}$ chains, aliphatic chains containing a terminal amino group and phenyl substituents. A particularly preferred adsorbent is phenyl-substituted agarose, known by the tradename, Phenyl-Sepharose, which includes benzene rings bonded to an agarose matrix.

The adsorbent is equilibrated in a manner similar to the equilibration of the cation-exchange resin using an equilibration buffer, for example, a phosphate buffer of appropriate pH and ionic strength. The hIL-6 sample obtained from the cation-exchange step is loaded onto the adsorption column and equilibration buffer is passed through the column until there is no further elution of sample components, as determined by UV absorbance at 280 nm. Elution of adsorbed hIL-6 from the adsorbent is carried out, in a gradient on non-gradient manner, using an elution buffer capable of interfering with the interaction between the hIL-6 and the adsorbent.

The hydrophobic chromatography step is desirably conducted at a temperature at which proteolytic breakdown of hIL-6 is minimized i.e. a temperature ranging from about 4° C. to 25° C. Preferably, this chromatographic step is conducted at a temperature at the lower end of this temperature rage, for example, at a temperature of between 4°–10° C., and most preferably at a temperature of 4° C. Accordingly, the adsorption column, equilibration and elution buffers and the hIL-6 sample are desirably cooled to the temperature at which the chromatography is to be conducted prior to their use in order to maintain a constant temperature during the chromatographic separation.

In a specific embodiment of the present invention, the hydrophobic chromatographic purification of hIL-6 was conducted at 4° C. The adsorption column contained phenyl-Sepharose adsorbent material. The column was equilibrated with a phosphate buffer having a pH of 7.5 and containing ammonium sulphate (1.5M). The technique of gradient elution was used to elute hIL-6 from the column with phosphate buffer of decreasing ammonium sulphate concentration. Specifically, the initial concentration of ammonium sulphate in the elution buffer was 1.5M and it was decreased to 0.2M ammonium sulphate over about 20 column volumes of buffer. Human IL-6 eluted from the column between 0.9M and 0.4M ammonium sulphate. The identity of hIL-6 was confirmed with RP-HPLC or SDS gel electrophoresis methods by reference to standards.

The order in which the cationic exchange and hydrophobic chromatographic steps are conducted in the purification of hIL-6 is not restricted and thus may be interchanged. The purity of the final essentially pure hIL-6 product is not effected when these steps are interchanged providing each step is conducted as set out herein. Thus, although cationic exchange may be the first step in the purification method, the step of hydrophobic chromatography may be conducted prior to the step of cationic exchange chromatography.

The final step in the present purification method is the reverse-phase high performance liquid chromatography step which separates proteins based on the principle of partitioning between the mobile and stationary liquid phases. RP-HPLC is conducted in the presence of a charge modifier or ion-pairing agent in order to attain human IL-6 that is essentially pure. Anionic and cationic charge modifiers are suitable for use in the RP-HPLC step of IL-6 purification and include, for example, the anionic charge modifiers trifluoroacetic acid, phosphoric acid and heptafluorobutyric acid and the cationic charge modifiers, for example, amine-based agents such as di- and tri-lower alkyl amines including trimethylamine, triethylamine, tributylamine and di-propylamine. Such cationic charge modifiers may be used in salt form, for example, triethylamine phosphate, prepared by mixing approximately equal amounts of triethylamine and phosphoric acid. Furthermore, the charge modifier may be formulated in an alkanol solvent, such as methanol, propanol or isopropanol, if desired, or in an organic acid such as formic acid.

Particularly preferred charge modifiers for use in purifying hIL-6 are the cationic charge modifiers, such as triethylamine in salt form, as the conditions of the RP-HPLC separation in the presence of a cationic charge modifier are superior to those conducted in the presence of an anionic charge modifier. For example, the separation of hIL-6 is effected more efficiently in the presence of a cationic charge modifier, leading to reduced HPLC-processing time. It is desirable, when a salt of an amine-based charge modifier is used, to remove the charge modifier by desalting the material collected from the RP-HPLC column as a further step in the IL-6 purification method. Desalting can be performed by subjecting the collected sample to any one of a variety of suitable desalting methods, such as gel filtration, ultrafiltration, or RP-HPLC in which a volatile charge modifier is employed such as trifluoroacetic acid (TFA) or heptafluoroacetic acid.

The mobile phase comprises two solvent solutions, a polar and a non-polar solvent, to be blended gradiently over the course of the HPLC run. The polar solvent, designated herein solvent "A", contains water and a charge modifier. The non-polar solvent, designated herein solvent "B", contains water, a charge modifier and an organic solvent, such as acetonitrile, methanol or propanol, in an amount of approximately 80%. The solvents are prepared by combining HPLC-grade components, then faltering using, for example, a 0.2 micron filter, and finally degassing to remove oxygen. The mount of charge modifier in each of solvent "A" and solvent "B" varies with the particular charge modifier to be used and may be present in an amount of about 0.02% to 2.0% by volume. The preferred mount by volume of the charge modifier, TFA, in the mobile phase is about 0.1%, while the preferred mount of the charge modifiers, triethylamine phosphate and phosphoric acid, is about 1.0% and 0.12%, respectively.

The hIL-6-containing fractions obtained from the adsorption chromatography purification step are combined, adjusted to a pH of about 4.0 and injected onto an RP-HPLC column pre-equilibrated with a mobile phase of the appropriate gradient. The appropriate gradient will vary with a number of factors including the nature of solvents "A" and "B", the charge modifier to be used and the column. Reverse-phase HPLC columns suitable for hIL-6 purification include columns packed with silica beads bearing alkyl groups ranging in length from 4–18 carbon atoms, i.e. $C_4$–$C_{18}$. Preferably the column is packed with silica having attached thereto $C_{18}$ alkyl groups. Thus, when TFA is the charge modifier, the column may be equilibrated at a gradient of 62% A/38%B and subsequently altered during the HPLC run to respective gradients of 44%A/56% B, 40% A/60% B and 35% A/65% B before returning to the equilibrating concentrations of A and B. Under these conditions, essentially pure hIL-6 elutes from the column at 45 minutes in 40% A/60% B.

In accordance with a further aspect of the present invention, a pharmaceutical composition containing essentially pure human IL-6 is provided. Such compositions can be in any form suitable for administration, including tablets, pills, capsules, powders, aerosols, suppositories, creams, lotions, ointments, skin patches, parenterals, oral liquids such as suspensions, solutions and emulsions, ophthalmic liquids and injectable liquids. The preferred administrable form of the hIL-6 will depend on its intended therapeutic use, which may include the treatment of bacterial and vital infections, tumours, immunodeficiency diseases, bone marrow deficiencies, and shock syndromes, as disclosed in U.S. patent application No. 07/612,675 to the National Institute of Health and PCT Application No. WO 88/00206 to Genetics Institute, Inc.

The present hIL-6-containing pharmaceutical composition comprises a therapeutically effective mount of essentially pure hIL-6. The term "therapeutically effective amount" is used herein to denote an mount of the composition indicated for a given treatment while not exceeding an mount which may cause significant adverse effects.

The composition additionally comprises a pharmaceutically acceptable carrier. As used herein, the term "pharmaceutically acceptable" means acceptable for use in the pharmaceutical and veterinary arts, and not being toxic or otherwise unacceptable. The nature of the carrier will depend on both the intended therapeutic use of the composition and the mode of administration suitable for that use. Thus, compositions to be administered orally are prepared using carriers that are suitably combined with IL-6 for oral ingestion, including but not limited to sugars, starches, cellulose and derivatives thereof, wetting agents, lubricants such as sodium lauryl sulfate, stabilizers, tabletting agents, anti-oxidants, preservatives, colouring agents and flavouring agents; while compositions to be administered by injection are prepared by combination with liquid carriers including, for example, buffered or physiological saline solutions.

Further, the hIL-6 compositions according to the present invention may contain a second therapeutic agent, if desired, to enhance the therapeutic effect of hIL-6. For example, pharmaceutical compositions containing IL-6 and the IL-6 receptor, which has been designated IFN-β/IL-6-R, or containing IL-6 and the soluble extracellular fragment or salts of the IL-6 receptor or functional derivatives, precursors or active fractions thereof, have been described in published European Application No. 413 908. Such compositions have been found to have enhanced IL-6 activity in the treatment of conditions such as bacterial infection, burns and trauma.

Specific embodiments of the present invention are described in detail in the following specific examples which are not to be construed as limiting:

Example 1—Production of Human IL-6

Recombinant human IL-6 was produced by a fungal expression system, specifically, using *Aspergillus nidulans* essentially as described by Contreras et al. in Biotechnology, 1991, 9:378, incorporated herein by reference. Briefly, A. nidulans was transformed with an expression vector encoding a fusion protein comprising the *A. niger* glucoamylase (glaA) structural gene, a spacer peptide containing a KEX-2 like processing signal and hIL-6 cDNA. This fusion protein was under the control of an alcA promoter. IL-6 was produced as a glucoamylase-kex2-hIL6 fusion protein which was cleaved in situ at the KEX-2 like fusion site by an indigenous fungal protease, releasing mature hIL-6 into the culture supernatant.

The hIL-6-containing fungal broth was filtered using Mira-cloth to render a broth having a pH of between 7.8–8.0 and a conductivity of 12–16 Ms/cm. The protein concentration of the broth was 0.15–0.22 mg/ml, as determined using the conventional Bradford assay with a bovine serum albumin (BSA) standard. Example 2— Cation Exchange Chromatographic Purification of IL-6

The pH of the IL-6-containing fungal broth was adjusted to a pH of 4.5 by the addition of glacial acetic acid and the conductivity of the broth was adjusted to 8.0 Ms/cm by the addition of deionized water prior to its loading onto the column.

A 5×5 cm (100 ml bed volume) S-Sepharose fast-flow (Pharmacia) column equilibrated with acetate equilibration buffer (25 mM, pH 4.5) was used for the purification of IL-6 from the fungal broth. A sample of the fungal broth containing 15–20 mg protein per ml of gel was loaded onto the equilibrated column. Following loading, the column was washed with 3 column volumes of a first acetate wash buffer (25 mM, pH 4.5) and then with a second acetate wash buffer (25 mM, pH 5.5) until the $A_{280}$ was approaching zero. Each of the wash buffers were flowed through the column at a rate of 8 ml/min. IL-6 was eluted from the column at a flow rate of 8 ml/min using approximately 3–4 column volumes of phosphate elution buffer (50 mM, pH 7.5).

Elution of hIL-6 was confirmed by RP-HPLC analysis by reference to standards, using the method described in Example 4. Human IL-6-containing fractions were combined.

Example 3—Hydrophobic Chromatographic Purification of IL-6

To the hIL-6 eluate from the cation exchange chromatography step was added solid ammonium sulphate to a final concentration of 1.5M. The pH of the eluate was adjusted to pH 7.5 using sodium hydroxide (2M).

A 2.5×15 cm (74 ml bed volume) low substitution Phenyl-Sepharose fast-flow (Pharmacia) column equilibrated with phosphate buffer containing ammonium sulphate (pH 7.5, 50 mM phosphate, 1.5M ammonium sulphate) was used. The equilibrated column was loaded with the eluate at a rate of 5 ml/min. Following loading, the column was washed with a first phosphate wash buffer (pH 7.5, 50 mM) containing ammonium sulphate (1.5M) until $A_{280}$ approached zero. IL-6 was gradiently eluted from the column by washing the column with a second phosphate wash buffer (pH 7.5, 50 mM) containing a decreased ammonium sulphate concentration (0.2M). IL-6 eluted from the column at an ammonium sulphate concentration of between 0.9M and 0.4M (approximately 20 column volumes of buffer or 1.48 L of buffer).

Elution of hIL-6 was confirmed by RP-HPLC analysis by reference to standards, using a method described in Example 4. Human IL-6-containing fractions were combined.

Example 4—Reverse-phase HPLC Purification of IL-6

Essentially pure IL-6 was obtained by subjecting the hIL-6 adsorption chromatography eluate, adjusted to pH 4.0 by addition of phosphoric acid, to a final reverse-phase chromatography step in the presence of a charge modifier. A Water's HPLC 820 computerized system having two 510 gradient pumps, Waters Wisp autoinjector and Hewlett Packard 1040 scanning diode array detector was used for the analysis including a Water's MicroBondapak C18 column (125 Å, 10 μm particle size, 3.9×300 mm). The mobile phase comprised a first solvent (A) of water containing 1.0% (v/v) triethylamine and 1.2% phosphoric acid (70% v/v) and a second solvent (B) of acetonitrile (80% v/v with water) containing 1.0% triethylamine and 1.2% phosphoric acid (70% v/v). The column was equilibrated with 61% A/39% B mobile phase gradient. A sample of up to 5 ml was injected into the column and the following mobile phase gradient was used to elute IL-6:

| Time | % A | % B |
|------|-----|-----|
| 0    | 61  | 39  |
| 1    | 61  | 39  |
| 6    | 48  | 52  |
| 22   | 44  | 56  |
| 54   | 40  | 60  |
| 59   | 61  | 39  |
| 65   | 61  | 39  |

IL-6 eluted at 38.5 minutes as indicated by an absorbance peak at 214 nm. In particular, the IL-6 eluted at about 56% solvent B (acetonitrile).

An alternative mobile phase was also used to purify the IL-6 sample. Solvent A of this mobile phase comprised water containing 0.1% (v/v) TFA and solvent B comprised acetonitrile (80% v/v with water) containing 0.086% (v/v) TFA. The solvent gradient employed was as follows:

| Time | % A | % B |
|------|-----|-----|
| 0    | 62  | 38  |
| 1    | 62  | 38  |
| 7    | 44  | 56  |
| 23   | 40  | 60  |
| 63   | 35  | 65  |
| 67   | 62  | 38  |
| 72   | 62  | 38  |

IL-6 eluted at 45 minutes as indicated by an absorbance peak at 214 nm. In particular, the IL-6 eluted at about 60% solvent B (acetonitrile).

A further alternative mobile phase was used to puffy the IL-6 in which solvent A was water containing 0.12% phosphoric acid and solvent B was acetonitrile containing 0.12%. The gradient employed was as follows:

| Time | % A | % B |
|------|-----|-----|
| 0    | 62  | 38  |
| 1    | 62  | 38  |
| 6    | 52  | 48  |
| 22   | 48  | 52  |
| 54   | 44  | 56  |
| 59   | 62  | 38  |
| 64   | 62  | 38  |

IL-6 eluted at 45 minutes as indicated by an absorbance peak at 214 nm. In particular, the IL-6 eluted at about 52% solvent B (acetonitrile).

The flow rate of the mobile phase through the column in each case was 1 ml/min and column temperature was maintained at 30° C. The pH of the mobile phase in each case was adjusted to pH 2.0–2.1.

The eluting IL-6 was collected for confirmation of purity using capillary electrophoresis.

Example 5—Analysis of hIL-6 by Capillary Electrophoresis

Purity of the IL-6 samples obtained by the TFA-, TEA- and phosphoric acid-based RP-HPLC techniques described in Example 4 were evaluated using the more sensitive analytical technique of capillary electrophoresis. For this purpose, the Biorad CE 3000 capillary electrophoresis device was used fitted with an uncoated capillary (50×50 cm) pre-conditioned with phosphate buffer (10 mm, pH 2.5). The operating conditions used to conduct the analyses included a voltage of 10 Kv and a column temperature of 20° C.

Figure 3:
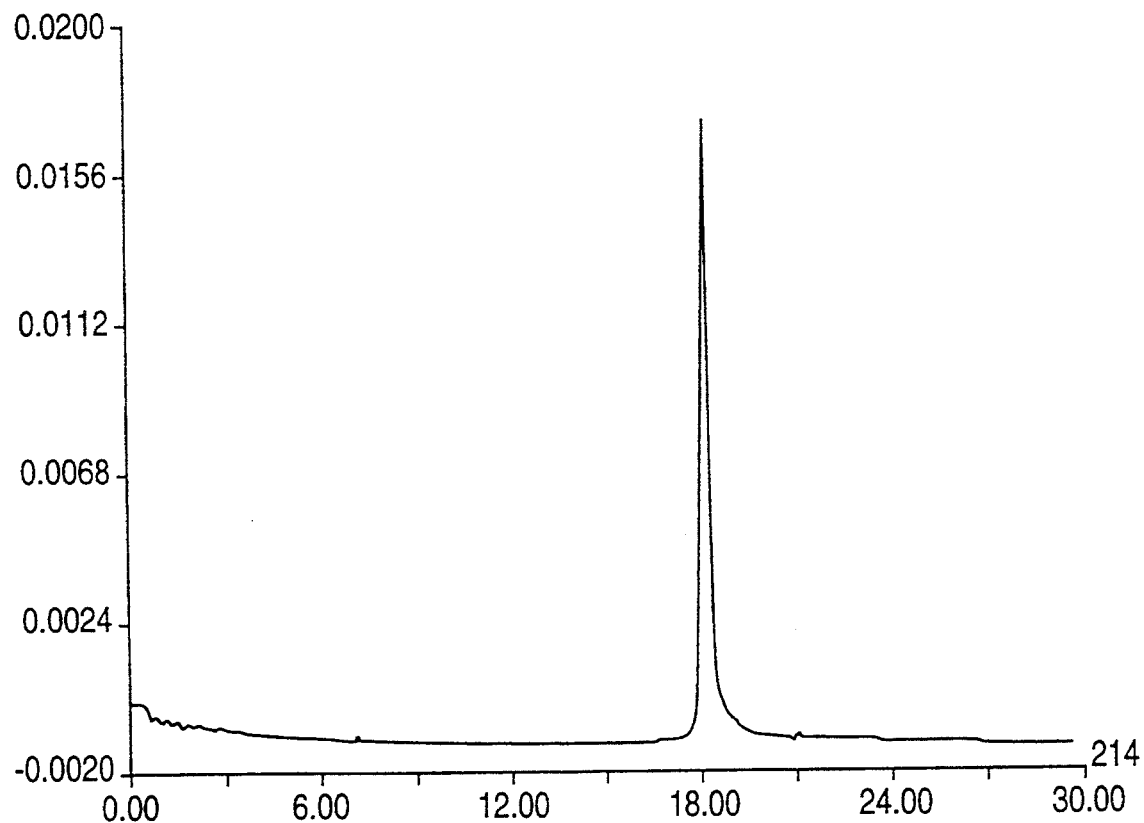
FIG. 3 represents the absorbance ($A_{214}$) capillary electrophoretic profile of essentially pure human interleukin-6 obtained using trifluoroacetic acid-based RP-HPLC.
Figure 4:
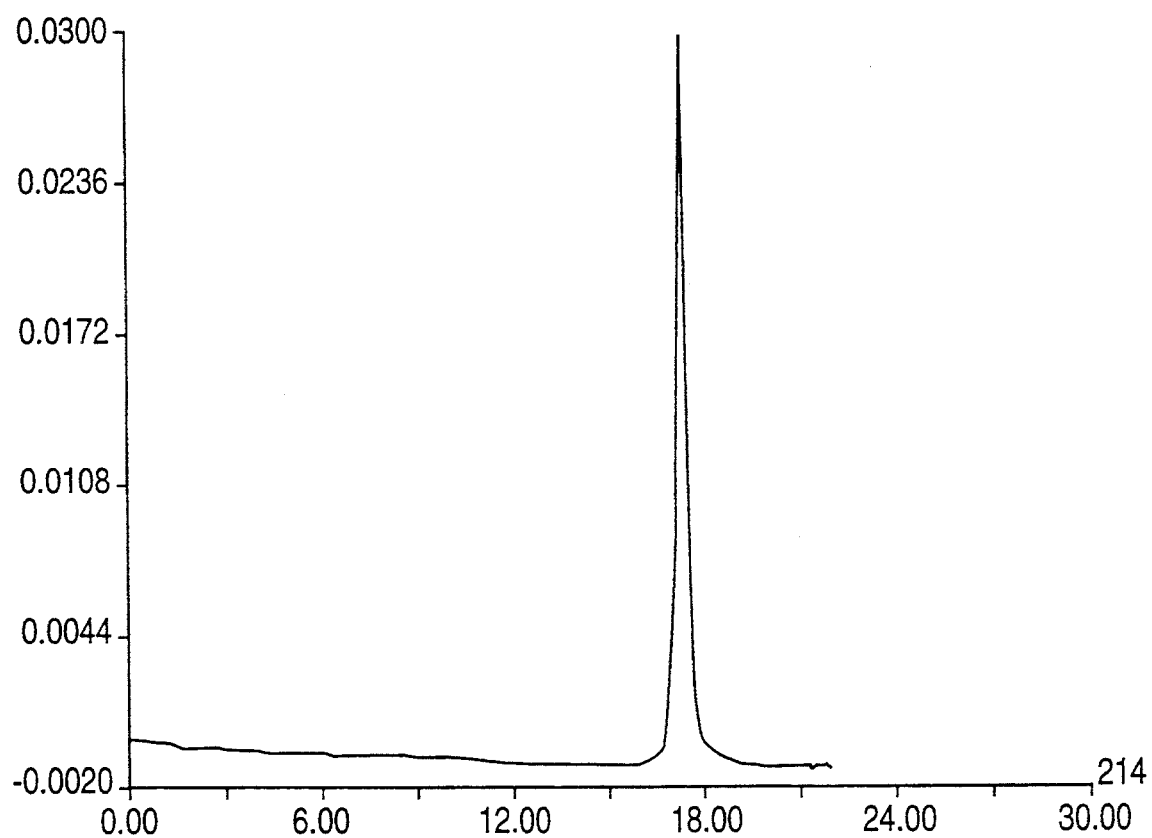
FIG. 4 represents the absorbance ($A_{214}$) capillary electrophoretic profile of essentially pure human interleukin-6 obtained using phosphoric acid-based RP-HPLC.

Prior to conducting each analysis, the IL-6 samples were lyophilised and then desalted using any one of several conventional desalting techniques as outlined herein. The samples were reconstituted in phosphate buffer (10 mM, pH 2.5) to give a final concentration of between 0.2 and 1.0 mg/mL. Each sample was injected onto the column at a pressure of between 5–10 psi/sec and in each case single peak absorption at 214 nm was obtained, as illustrated in FIGS. 2, 3 and 4, indicating that each IL-6 sample was essentially pure.

We claim:

1. A method for obtaining essentially pure human interleukin-6 comprising the steps of:
   1) fractionating a preparation containing human interleukin-6 by cation-exchange chromatography using a column comprising a cationic resin, and eluting from said column a first interleukin-6 sample;
   2) fractionating said first interleukin-6 sample by hydrophobic chromatography using an adsorption column comprising a hydrophobic adsorbent, and eluting from said adsorption column a second interleukin-6 sample;
   3) fractionating said second interleukin-6 sample by reverse-phase high performance liquid chromatography in the presence of a cationic charge modifier; and
   4) collecting essentially pure human interleukin-6: wherein steps 1) and 2) are interchangeable.

2. A method as defined in claim 1, comprising the further step of desalting the interleukin-6 obtained from the reverse-phase liquid chromatographic step.

3. A method as defined in claim 1, wherein said preparation comprises non-glycosylated human interleukin-6.

4. A method as defined in claim 1, wherein said hydrophobic adsorbent is phenyl-substituted agarose.

5. A method as defined in claim 1, wherein said charge modifier is amine-based charge modifier.

6. A method as defined in claim 5, wherein said amine-based charge modifier is triethylamine, or a salt thereof.

7. A method as defined in claim 1, wherein said preparation containing interleukin-6 is derived from a microbial source.

8. A method as defined in claim 7, wherein said microbial source is a fungal source of interleukin-6.

9. A method as defined in claim 8, wherein said fungal source is *Aspergillus nidulans*.

10. A method as claimed in claim 1, consisting essentially of the recited steps.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 183 amino acids
        ( B ) TYPE: amino acid
        ( D ) TOPOLOGY: linear ( x i ) SEQUENCE DESCRIPTION: SEQ ID NO:1:

```
Val  Pro  Pro  Gly  Glu  Asp  Ser  Lys  Asp  Val  Ala  Ala  Pro  His  Arg  Gln
  1                 5                      10                         15

Pro  Leu  Thr  Ser  Ser  Glu  Arg  Ile  Asp  Lys  Gln  Ile  Arg  Tyr  Ile  Leu
                    20                      25                         30

Asp  Gly  Ile  Ser  Ala  Leu  Arg  Lys  Glu  Thr  Cys  Asn  Lys  Ser  Asn  Met
               35                      40                      45

Cys  Glu  Ser  Ser  Lys  Glu  Ala  Leu  Ala  Glu  Asn  Asn  Leu  Asn  Leu  Pro
```

```
              50                      55                          60
    Lys  Met  Ala  Glu  Lys  Asp  Gly  Cys  Phe  Gln  Ser  Gly  Phe  Asn  Glu  Glu
    65                      70                      75                           80

Thr  Cys  Leu  Val  Lys  Ile  Ile  Thr  Gly  Leu  Leu  Glu  Phe  Glu  Val  Tyr
                        85                           90                      95

Leu  Glu  Tyr  Leu  Gln  Asn  Arg  Phe  Glu  Ser  Ser  Glu  Glu  Gln  Ala  Arg
                   100                      105                      110

Ala  Val  Gln  Met  Ser  Thr  Lys  Val  Leu  Ile  Gln  Phe  Leu  Gln  Lys  Lys
                   115                      120                      125

Ala  Lys  Asn  Leu  Asp  Ala  Ile  Thr  Thr  Pro  Asp  Pro  Thr  Thr  Asn  Ala
         130                      135                      140

Ser  Leu  Leu  Thr  Lys  Leu  Gln  Ala  Gln  Asn  Gln  Trp  Leu  Gln  Asp  Met
    145                      150                      155                           160

Thr  Thr  His  Leu  Ile  Leu  Arg  Ser  Phe  Lys  Glu  Phe  Leu  Gln  Ser  Ser
                        165                      170                      175

Leu  Arg  Ala  Leu  Arg  Gln  Met
                   180
```

( 2 ) INFORMATION FOR SEQ ID NO:2:

( i ) SEQUENCE CHARACTERISTICS:
        ( A ) LENGTH: 525 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

```
GTAGCCGCCC  CACACAGACA  GCCACTCACC  TCTTCAGAAC  GAATTGACAA  ACAAATTCGG     60

TACATCCTCG  ACGGCATCTC  AGCCCTGAGA  AAGGAGACAT  GTAACAAGAG  TAACATGTGT    120

GAAAGCAGCA  AAGAGGCACT  GGCAGAAAAC  AACCTGAACC  TTCCAAAGAT  GGCTGAAAAA    180

GATGGATGCT  TCCAATCTGG  ATTCAATGAG  GAGACTTGCC  TGGTGAAAAT  CATCACTGGT    240

CTTTTGGAGT  TTGAGGTATA  CCTAGAGTAC  CTCCAGAACA  GATTTGAGAG  TAGTGAGGAA    300

CAAGCCAGAG  CTGTGCAGAT  GAGTACAAAA  GTCCTGATCC  AGTTCCTGCA  GAAAAAGGCA    360

AAGAATCTAG  ATGCAATAAC  CACCCCTGAC  CCAACCACAA  ATGCCAGCCT  GCTGACGAAG    420

CTGCAGGCAC  AGAACCAGTG  GCTGCAGGAC  ATGACAACTC  ATCTCATTCT  GCGCAGCTTT    480

AAGGAGTTCC  TGCAGTCCAG  CCTGAGGGCT  CTTCGGCAAA  TGTAG                    525
```